United States Patent
O'Donnell

(10) Patent No.: US 11,759,449 B2
(45) Date of Patent: Sep. 19, 2023

(54) METHODS FOR REDUCING OXIDATIVE EFFECTS OF FREE RADICALS

(71) Applicant: Hugg LLC, Las Vegas, NV (US)

(72) Inventor: Dennis M. O'Donnell, Basking Ridge, NJ (US)

(73) Assignee: HUGG LLC, Las Vegas, NV (US)

( * ) Notice: Subject to any disclaimer, the term of this patent is extended or adjusted under 35 U.S.C. 154(b) by 71 days.

(21) Appl. No.: 17/516,986

(22) Filed: Nov. 2, 2021

(65) Prior Publication Data
US 2023/0137695 A1 May 4, 2023

(51) Int. Cl.
| | | |
|---|---|---|
| A61K 31/37 | (2006.01) | |
| A61P 39/06 | (2006.01) | |
| A61K 47/22 | (2006.01) | |
| A61K 31/05 | (2006.01) | |

(52) U.S. Cl.
CPC ............ *A61K 31/37* (2013.01); *A61K 31/05* (2013.01); *A61K 47/22* (2013.01); *A61P 39/06* (2018.01)

(58) Field of Classification Search
CPC ........ A61K 31/37; A61K 31/05; A61K 47/22; A61P 39/06
See application file for complete search history.

(56) References Cited

U.S. PATENT DOCUMENTS

| | | | |
|---|---|---|---|
| 9,072,679 B2 | 7/2015 | Heggie et al. | |
| 10,413,524 B2 * | 9/2019 | Pezzuto | A23K 50/40 |
| 11,026,917 B2 | 6/2021 | Pezzuto | |
| 2007/0190209 A1 | 8/2007 | Sinnott | |
| 2017/0354638 A1 | 12/2017 | Veillet et al. | |
| 2020/0214330 A1 | 7/2020 | Demichele et al. | |

OTHER PUBLICATIONS

International Search Report and Written Opinion in corresponding PCT Application No. PCT/US2022/048153 dated Jan. 27, 2023.
National Cancer Institute. Antioxidants and Cancer Prevention, 7 pages https://www.cancer.gov/about-cancer/causes-prevention/risk/diet/antioxidants-fact-sheet.
Abdullah Shaito et al., Potential Adverse Effects of Resveratrol: A Literature Review. Int J Mol Sci. Mar. 2020; 21(6): 2084, 26 pages.
Bahare Salehi et al., Resveratrol: A Double-Edged Sword in Health Benefits. Biomedicines. Sep. 2018; 6(3): 91., 20 pages.
Ruiqing Chen, et al. Potential toxicity of quercetin: The repression of mitochondrial copy number via decreased POLG expression and excessive TFAM expression in irradiated murine bone marrow. Toxicol Rep. 2014; 1: pp. 450-458.
Leanne M Mathew, et al. Resveratrol administration increases phagocytosis, decreases oxidative burst, and promotes pro-inflammatory cytokine production in healthy dogs. Vet Immunol Immunopathol. Sep. 2018;203: pp. 21-29. doi: 10.1016/j.vetimm.2018.07.013.
Natural Dog Health Remedies. Resveratrol Benefits to Dogs. Accessed on Oct. 13, 2021, 11 pages https://www.natural-dog-health-remedies.com/resveratrol-benefits.html.
Katie Woodley, Quercetin for Dogs: Uses and Benefits. Accessed on Oct. 13, 2021, 14 pages https://www.greatpetcare.com/wellness/quercetin-for-dogs-uses-and-benefits/.
M. Saljoughian, PharmD, PhD, Natural Powerful Antioxidants. US Pharm. 2007;1:HS38-HS42. Published Jan. 23, 2007, 17 pages. https://www.uspharmacist.com/article/natural-powerful-antioxidants.
Ask Ariel. Resveratrol for Dogs. Accessed on Oct. 13, 2021, 13 pages. https://www.askariel.com/resveratrol-for-dogs-p/149.htm.
Purina. Can Dogs Eat Grapes? Accessed on Oct. 13, 2021, 2 pages. https://www.purina.com/articles/dog/nutrition/can-dogs-eat-grapes.
Brendan Howard. Why Grapes & Raisins Are So Dangerous for Dogs. Aug. 24, 2020. 3 pages. https://www.dailypaws.com/dogs-puppies/nutrition/what-can-dogs-eat/can-dogs-eat-grapes.
Mary U. Ememe, et al. Evaluation of Resveratrol Supplementation on Laboratory Animals, Cats, Pigs, Horses, Dogs, Cattle, and Birds. Published: Nov. 5, 2018. DOI: 10.5772/intechopen.79104. 21 pages, Accessed at: https://www.intechopen.com/chapters/62407.
Rodney Habib. Nature's Benadryl: Quercetin. Apr. 24, 2020, 11 pages. https://www.dogsnaturallymagazine.com/natures-benadryl-quercetin.
Resvantage Canine—Supplemental Facts & Ingredients. Accessed on Oct. 13, 2021, 2 pages. https://resveratroldogcancer.com/html/ingredients.shtml.
Tamara P. Kondratyuk, et al. Evidence supporting the conceptual framework of cancer chemoprevention in canines. *Sci Rep.* 2016; 6: 26500. Published online May 24, 2016. doi: 10.1038/srep26500, 13 pages.
National Institutes of Health. Antioxidants: In Depth. Updated: Nov. 2013, 8 pages. https://www.nccih.nih.gov/health/antioxidants-in-depth.
The Chocolate Trader. The 5 Proven Health Benefits of Eating Dark Chocolate. Accessed on Oct. 13, 2021, 3 pages. https://thechocolatetrader.com/dark-chocolate-5-health-benefits.

* cited by examiner

*Primary Examiner* — Timothy R Rozof
(74) *Attorney, Agent, or Firm* — LEASON ELLIS LLP

(57) ABSTRACT

Methods for reducing the oxidative effects of free radicals in an animal subject are described herein. Resveratrol, ellagic acid, and quercetin can be administered as a single composition to the animal subject, wherein the mass ratio of resveratrol, ellagic acid, and quercetin in the composition is 1:4:20.

14 Claims, 3 Drawing Sheets

Fig. 3

| | Quercetin | Resveratrol | Pomegranate | C1111 | C11020 |
|---|---|---|---|---|---|
| Replicate 1 | 2.66 | 0.76 | 0.53 | 0.88 | 1.45 |
| Replicate 2 | 2.39 | 0.73 | 0.57 | 0.89 | 1.48 |
| Replicate 3 | 2.71 | 0.73 | 0.51 | 0.90 | 1.52 |
| Ave | 2.58 | 0.74 | 0.54 | 0.89 | 1.48 |
| SD | 0.17 | 0.01 | 0.03 | 0.01 | 0.04 |

METHODS FOR REDUCING OXIDATIVE EFFECTS OF FREE RADICALS

FIELD

The present application relates to dietary compositions and methods of treatment, and in particular, dietary compositions and methods for reducing the oxidative effects of free radicals in subjects.

BACKGROUND

Free radicals (reactive oxygen species) accumulate in the bodies of mammals due to normal cell metabolism (e.g., adenosine triphosphate production) as well as external causes, such as pollution or radiation. While free radicals at low levels can provide some benefits to the body, high levels of free radicals can result in oxidative stress—an imbalance balance between the production of free radicals and the body's natural antioxidant defenses. Oxidative stress results in damage to the cells of the body, which can accelerate aging and increase the likelihood of developing certain chronic illnesses, such as cancers, cardiovascular disease, and neurodegenerative diseases.

Antioxidants can counteract some of the negative effects caused by free radicals in the body. Some antioxidants are naturally produced by the body, but additional antioxidants can be acquired by the body through diet. For instance, exogenous or dietary antioxidants such as lycopene, beta-carotene, and vitamins C and E, are found in various fruits, vegetables, and grains. Laboratory and animal studies suggest that increased levels of exogenous antioxidants can reduce free radical damage that is associated with cancer development (1).

Resveratrol is an exogenous antioxidant that can be found in foods such as grapes and blueberries in varying concentrations. Resveratrol has been shown in in vitro and in vivo studies to exhibit anti-inflammatory and anticarcinogenic properties (2). However, resveratrol has been shown to have poor solubility and bioavailability, and can exhibit toxicity at high doses (2, 3). As such, an effective but safe dosage of resveratrol has been difficult to determine.

Quercetin is a plant-based flavonol found in certain foods and vegetables and has been shown to have anti-inflammatory and anti-histamine characteristics. However, recent studies have suggested that quercetin can also have pro-oxidant effects, including mutagenic and cytotoxic effects, depending on the administered dosage (4).

U.S. Pat. Nos. 10,413,524 ("the '524 Patent") (5) and 11,026,917 ("the '917 Patent") (6) to John Michael Pezzuto discloses antioxidative stress compositions, such as dog biscuits and dietary supplements. These compositions can include at least 3 of the following compounds: resveratrol, genistein, curcumin, and quercetin. In at least one embodiment, the compounds of the '524 Patent and '917 patent can include ellagic acid. As much as 1500 mg of resveratrol can be included in each dog biscuit of the '524 Patent and '917 patent and resveratrol can make up as much as 80% by weight of the composition. However, the '524 and '917 patents do not take into account the potential toxicity of high doses of resveratrol or its potential bioavailability and solubility deficiencies.

As such, there is a need for improved methods for combating oxidative stress that can avoid potential toxicity. These and other needs are addressed by the present application.

SUMMARY

In a first aspect, the present application relates to a method for reducing the oxidative effects of free radicals in an animal subject. The method comprises administering to the animal subject: (a) resveratrol in an amount of 1.25 mg-7.5 mg; (b) ellagic acid in an amount of 5 mg-30 mg; and (c) quercetin in an amount of 25 mg-150 mg. The mass ratio of resveratrol:ellagic acid: quercetin being administered to the animal subject is 1:4:20.

In some embodiments, the amount of resveratrol is 2.5 mg, the amount of ellagic acid is 10 mg, and the amount of quercetin is 50 mg.

In some embodiments, the amount of resveratrol is 5 mg, the amount of ellagic acid is 20 mg, and the amount of quercetin is 100 mg.

In some embodiments, the animal subject is a cat or a dog.

In some embodiments the resveratrol, ellagic acid, and quercetin are administered in an ingestible, solid composition. In further embodiments, the ingestible, solid composition further comprises at least one excipient selected from the group consisting of mixed tocopherols.

In some embodiments, the ellagic acid is administered in the form of a pomegranate extract comprising 40% to 70% concentration of ellagic acid.

In a second aspect, the present application relates to a method for reducing the oxidative effects of free radicals in an animal subject where the method comprises administering to the animal subject a liquid composition. The liquid composition comprises (a) resveratrol in an amount of 2.5 mg/mL; (b) ellagic acid in an amount of 10 mg/mL; and (c) quercetin in an amount of 50 mg/mL, where the mass ratio of resveratrol:ellagic acid: quercetin in the liquid composition is 1:4:20.

In some embodiments, the liquid composition is administered at a dosage of 0.5 mL. In some embodiments, the liquid composition is administered at a dosage of 1.0 mL. In some embodiments, the liquid composition is administered at a dosage of 1.5 mL. In some embodiments, the liquid composition is administered at a dosage of 2.0 mL.

In some embodiments, the animal subject is a cat or a dog.

In some embodiments, the liquid composition further comprises at least one excipient selected from the group consisting of mixed tocopherols.

BRIEF DESCRIPTION OF THE FIGURES

FIG. 3 shows a table displaying The TEAC values of each antioxidant test group for each of the three replicates for each group in accordance with one or more embodiments.

DETAILED DESCRIPTION

Figure 1:
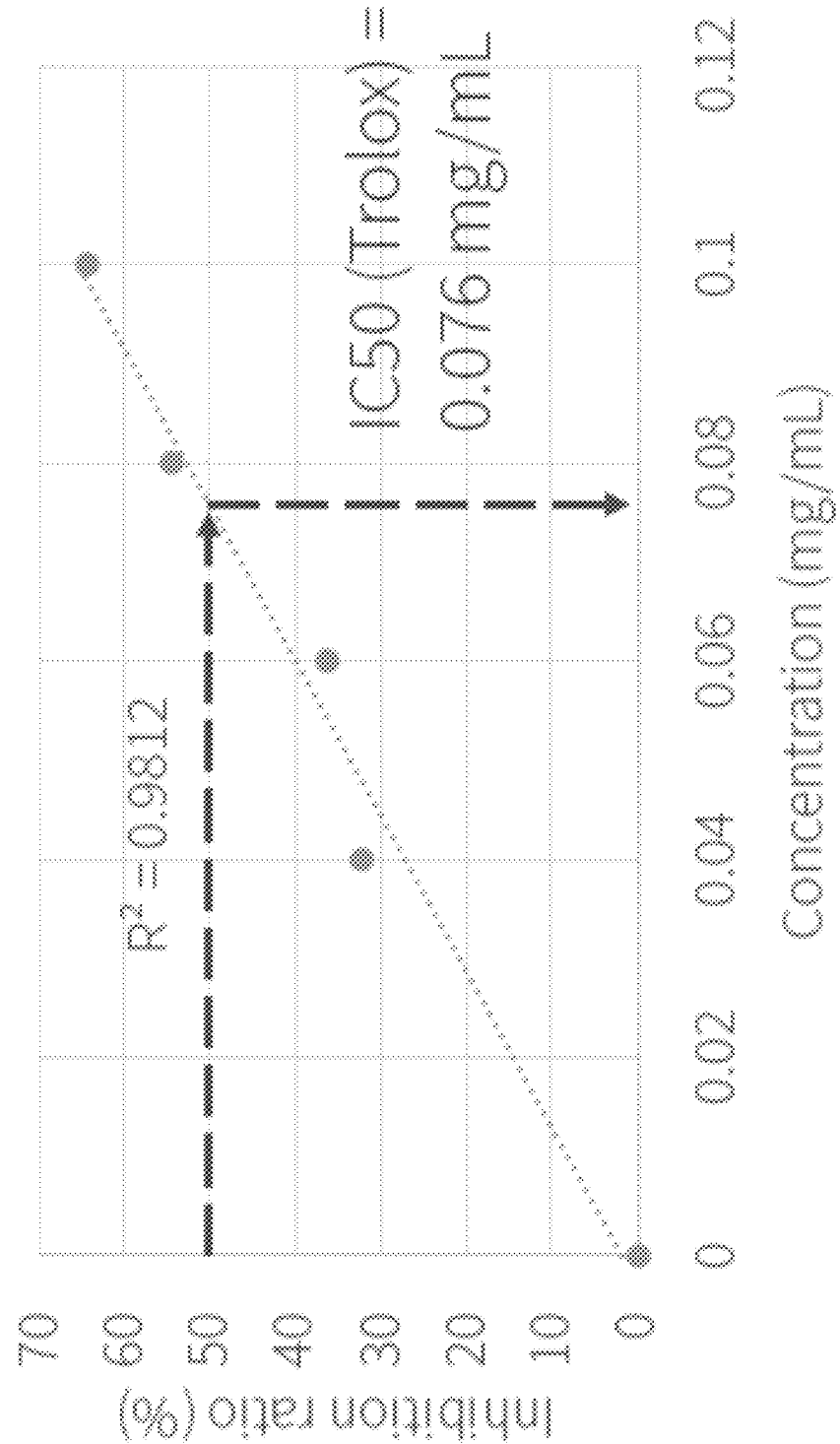
FIG. 1 displays an example calibration curve using a range of Trolox standard solutions in accordance with one or more embodiments.

Provided herein are methods for reducing the oxidative effects of free radicals in an animal subjects. In particular, in one or more embodiments, provided herein are methods for reducing the oxidative effects of free radicals in felines and canines. In the present methods, exogenous antioxidants including resveratrol, ellagic acid, and quercetin are administered to an animal subject, and these antioxidants act synergistically to reducing the oxidative effects of free radicals in the animal subject. In one or more embodiments, resveratrol, ellagic acid, and quercetin are administered to the animal subject in a single composition, such as a solid or liquid composition. These and other aspects of the present methods are described in further detail below.

In accordance with one or more embodiments, a method for reducing the oxidative effects of free radicals in an animal subject is provided in which resveratrol, ellagic acid, and quercetin are administered to an animal subject. As mentioned previously, resveratrol is an exogenous antioxidant that can be found in various foods and has been exhibited certain antioxidative effects. Quercetin is a plant-based flavonol found in certain foods and vegetables and has been shown to have anti-inflammatory and anti-histamine characteristics. Ellagic acid is another antioxidant found in different fruits and vegetables. In one or more embodiments of the present method, the resveratrol, ellagic acid, and quercetin are administered in a mass ratio of 1:4:20 (resveratrol: ellagic acid: quercetin). The administration of resveratrol, ellagic acid, and quercetin in this mass ratio provides a synergistic improvement in antioxidative effects without having to increase the resveratrol dosage to levels that can result in toxic effects on animal subjects.

In one or more embodiments, the resveratrol is administered in a solid formulation in an amount in the range of 1.25 mg to 7.5 mg. In at least one embodiment, the resveratrol is administered in a liquid formulation in an amount in the range of 1.25 mg/mL to 7.5 mg/mL. The resveratrol can be in a concentrated form (e.g., great than 99% pure) or can be provided in a fruit extract powder.

In one or more embodiments, the ellagic acid is administered in a solid formulation in an amount in the range of 5 mg to 30 mg. In at least one embodiment, the ellagic acid is administered in a liquid formulation in an amount in the range of 5 mg/mL to 30 mg/mL. The ellagic acid can be in concentrated form or in the form of fruit extract powder, such as a pomegranate extract (40%-70% concentration of ellagic acid).

In one or more embodiments, the quercetin is administered in a solid formulation in an amount in the range of 25 mg to 150 mg. In at least one embodiment, the quercetin is administered in a liquid formulation in an amount in the range of 25 mg/mL to 150 mg/mL. The quercetin can be in concentrated form or in the form of fruit extract powder.

In one or more embodiments, the resveratrol, ellagic acid, and quercetin can be administered to the animal subject as a single composition. The single composition can be an ingestible, solid composition, such as rapidly dissolving tablets and soft chews. For example, the single composition can be an ingestible, solid composition comprising 1.25 mg-7.5 mg of resveratrol, 5 mg-30 mg of ellagic acid, and 25 mg-150 mg quercetin and having a mass ratio of resveratrol: ellagic acid:quercetin of 1:4:20.

In one or more preferred embodiments, the animal subjects administered the composition are canines or felines (e.g., domesticated dogs and cats). In one or more embodiments, the amount of resveratrol, ellagic acid, and quercetin in the solid composition can vary depending on the size of the canine or feline. For instance, in one or more embodiments, for dogs and cats that weigh less than 25 pounds, the ingestible, solid composition can comprise 2.5 mg of resveratrol, 10 mg of ellagic acid, and 50 mg of quercetin. The amounts of resveratrol, ellagic acid, and quercetin can then be increased in larger dogs or cats. Specifically, in one or more embodiments, for dogs and cats that weigh 26-75 pounds, the ingestible, solid composition can comprise 5 mg of resveratrol, 20 mg of ellagic acid, and 100 mg of quercetin. Likewise, in one or more embodiments, for dogs and cats that weigh greater than 75 pounds, the ingestible, solid composition can comprise 7.5 mg of resveratrol, 30 mg of ellagic acid, and 150 mg of quercetin. In one or more embodiments, the solid composition can be in the form of ingestible (orally administered) dog or cat chews.

In certain embodiments, at least one of resveratrol, ellagic acid, and quercetin can be present in the solid composition in the form of a fruit or food extract powder, such as blueberry fruit powder, cranberry fruit powder, pomegranate extract, or peanut butter powder.

In some embodiments, the solid composition can comprise one or more additional ingredients, including but not limited to chamomile, thiamine mononitrate, calcium ascorbate, passion flower, ginger, L-tryptophan, glucosamine HCl, methylsulfonylmethane, *yucca* schidigera, chondroitin sulfate, omega-3 fatty acids, omega-6 fatty acids, melatonin, DL-alpha-tocopheryl acetate, turmeric root, grape seed extract, pumpkin powder, bromelain, eicosapentaenoic acid (EPA), and docosahexaenoic acid (DHA).

The solid composition can also include one or more excipients. In one or more embodiments, the excipients in the solid composition include one or more tocopherols. The one or more tocopherols are all forms of vitamin E, and can comprise d-alpha ($\alpha$), d-beta ($\beta$), d-gamma ($\gamma$), and d-delta ($\delta$) tocopherol. The tocopherols help maintain the freshness and shelf life of the composition and can also function as natural alternatives to synthetic antioxidants, such as butylated hydroxytoluene (BHT), butylated hydroxyanisole (BHA), and tert-Butylhydroquinone (TBHQ). As used herein, a combination of multiple tocopherols used in the compositions described in the present application are considered "mixed tocopherols."

One or more inactive ingredients can also be included in the solid composition, including but not limited to, apple cider vinegar, peanut butter, citric acid, sorbic acid, brewers dried yeast, canola oil, dried potato product, flaxseed, glycerin, natural flavoring, rosemary extract, sunflower lecithin, sunflower oil, tapioca starch, and water.

In at least one embodiment, the single composition comprising resveratrol, ellagic acid, and quercetin can be in the form of a liquid composition. In one or more embodiments, the liquid composition can comprise 2.5 mg/mL of resveratrol, 10 mg/mL of ellagic acid, and 50 mg/mL of quercetin. Similar to the solid composition, the dosage of liquid composition being administered to the canine or feline can vary depending on the size of the canine or feline. For instance, in one or more embodiments, for dogs and cats that weigh less than 10 pounds, the amount of liquid composition administered to the animal is 0.5 mL. The dosage can then be increased in larger dogs or cats. Specifically, in one or more embodiments, for dogs and cats that weigh 10-30 pounds, the amount of liquid composition administered to the animal is 1.0 mL. In one or more embodiments, for dogs and cats that weigh greater than 31-65 pounds, the amount of liquid composition administered to the animal is 1.5 mL. Likewise, in one or more embodiments, for dogs and cats that weigh greater than greater than 65 pounds, the amount of liquid composition administered to the animal is 2.0 mL. In one or more embodiments, the liquid composition can be in the form of an ingestible (orally administered) concentrated liquid for a dog or a cat.

In certain embodiments, at least one of resveratrol, ellagic acid, and quercetin can be present in the liquid composition in the form of a fruit or food extract powder, such as blueberry fruit powder, cranberry fruit powder, pomegranate extract, or peanut butter powder.

In some embodiments, the liquid composition can comprise one or more additional ingredients, including but not limited to glucosamine HCl, perna canaliculus, chondroitin sulfate, ascorbic acid (vitamin C), manganese, methylsulfonylmethane, crude fat, omega-3 fatty acids, omega-6 fatty acids, fish oil, cod oil, eicosapentaenoic acid (EPA), docosahexaenoic acid (DHA), GHA, sunflower seed oil, hemp seed oil, salmon oil, flax seed oil, *Bifidobacterium bifidum, Lactobacillus acidophilus, Lactococcus lactis, Bifidobacterium lactis*, elderberry, milk thistle, pumpkin, olive leaf, *echinacea*, turmeric, zinc, iron, calcium, copper, vitamin A, vitamin D3, iodine, niacin, potassium, methionine, phosphorous, magnesium, thiamine (vitamin B1), riboflavin (vitamin B2), pantothenic acid, pyridioxide (vitamin B6), folic acid, and vitamin B12.

One or more inactive ingredients can also be included in the liquid composition, including but not limited to purified water, glycerin, and flavoring.

The liquid composition can also include one or more excipients including one or more tocopherols and/or vitamin E. The one or more tocopherols can comprise d-alpha ($\alpha$), d-beta ($\beta$), d-gamma ($\gamma$), and d-delta ($\delta$) tocopherol.

The methods of the present application reduce the oxidative effects of free radicals in an animal subject. Moreover, the mass ratio of resveratrol, ellagic acid, and quercetin (1:4:20) provides a synergistic antioxidative effect on the animal subjects. Specifically, it was determined that the administration of resveratrol, ellagic acid, and quercetin in a mass ratio of 1:4:20 results in dramatically increased antioxidative activity as compared with administration of resveratrol, ellagic acid, and quercetin in a mass ratio of 1:1:1. Accordingly, the mass ratio of 1:4:20 for resveratrol, ellagic acid, and quercetin enables the present method to utilize lower dosages of resveratrol to avoid the toxic effects associated with high doses of resveratrol. In other words, the present method utilizes lower dosages of resveratrol to avoid toxic effects, but can maintain the antioxidant efficacy of associated with resveratrol. Additionally, by using a combination of resveratrol, ellagic acid, and quercetin, the present methods use lower dosages of quercetin, which has also been associated with toxic effects at higher doses (4). This mass ratio also results in antioxidative effects that are greater than those provided by resveratrol or ellagic acid alone.

The present invention may be better understood by reference to the following non-limiting examples, which are presented in order to more fully illustrate the preferred embodiments of the present application. They should in no way be construed to limit the broad scope of the invention.

EXAMPLES

The following examples evaluated the antioxidant capacity of three antioxidants samples and the combination of the three antioxidants in various mass ratios using a DPPH (2,2-diphenyl-1-picrylhydrazyl) antioxidant assay. These examples are described in further detail below with reference to the accompanying drawing figures.

Antioxidant Capacity Assays
Materials and Methods

The following samples of resveratrol, ellagic acid, and quercetin were provided: resveratrol (>99% pure), Sigma, R5010 Lot #SLCG4677; Pomegranate PE (Aunutra®, Lot #PH210702) containing 40% ellagic acid; and quercetin, Sigma, PHR1488, Source #LRA87780.

Sample preparation: samples were weighted and dissolved in ethanol (99.5%, Fisher Scientific AC615095000) at a concentration of 1 mg/mL. Pomegranate PE (40% ellagic acid) contained insoluble debris that affected assay readings. Thus, the sample was filtrated through a 0.45 μm nylon filter, and the filtrate was used for the determination of antioxidant capacity. The assay results are based on the assumption that the filtration step did remove a significant amount of ellagic acid.

Preliminary Experiments: dilutions were made for each test group and the inhibition ratio percentage was calculated with the DPPH Antioxidant Assay Kit (Dojindo, D678) per manufacturer's instructions. This step was required to narrow down the concentrations required to calculate $IC_{50}$.

Measurement of Antioxidant Capacity: samples were run again using the concentrations determined in the preliminary experiment and the $IC_{50}$ for each sample was calculated. 3 replicates were used for this assay per test group and concentration.

Trolox Equivalent Antioxidant Capacity (TEAC) determination: comparison against $IC_{50}$ from Trolox calibration curve provided in the DPPH Antioxidant Assay Kit (Dojindo, D678) as indicated in the following equation: $TEAC = IC_{50} (Trolox)/IC_{50} (sample)$.

Instrumentation: absorbance for each sample was measured at 560 nm (at room temperature, no shaking) with a Benchmark Scientific Accuris SmartReader MR9600.

Trolox equivalent activity (TEAC) values from the three antioxidants (resveratrol, pomegranate extract [40% ellagic acid], and quercetin) and two combinations with mass ratios of 1:10:20 and 1:1:1 for resveratrol, pomegranate extract and quercetin, respectively by comparison with a Trolox calibration curve. It is noted that the test group having a mass ratio of resveratrol, pomegranate extract, and quercetin of 1:10:20 is equivalent to a composition of the present application having a mass ratio of 1:4:20 for resveratrol, ellagic acid, and quercetin (as described above) as the pomegranate extract in the present examples is 40% ellagic acid.

Results

Figure 2:
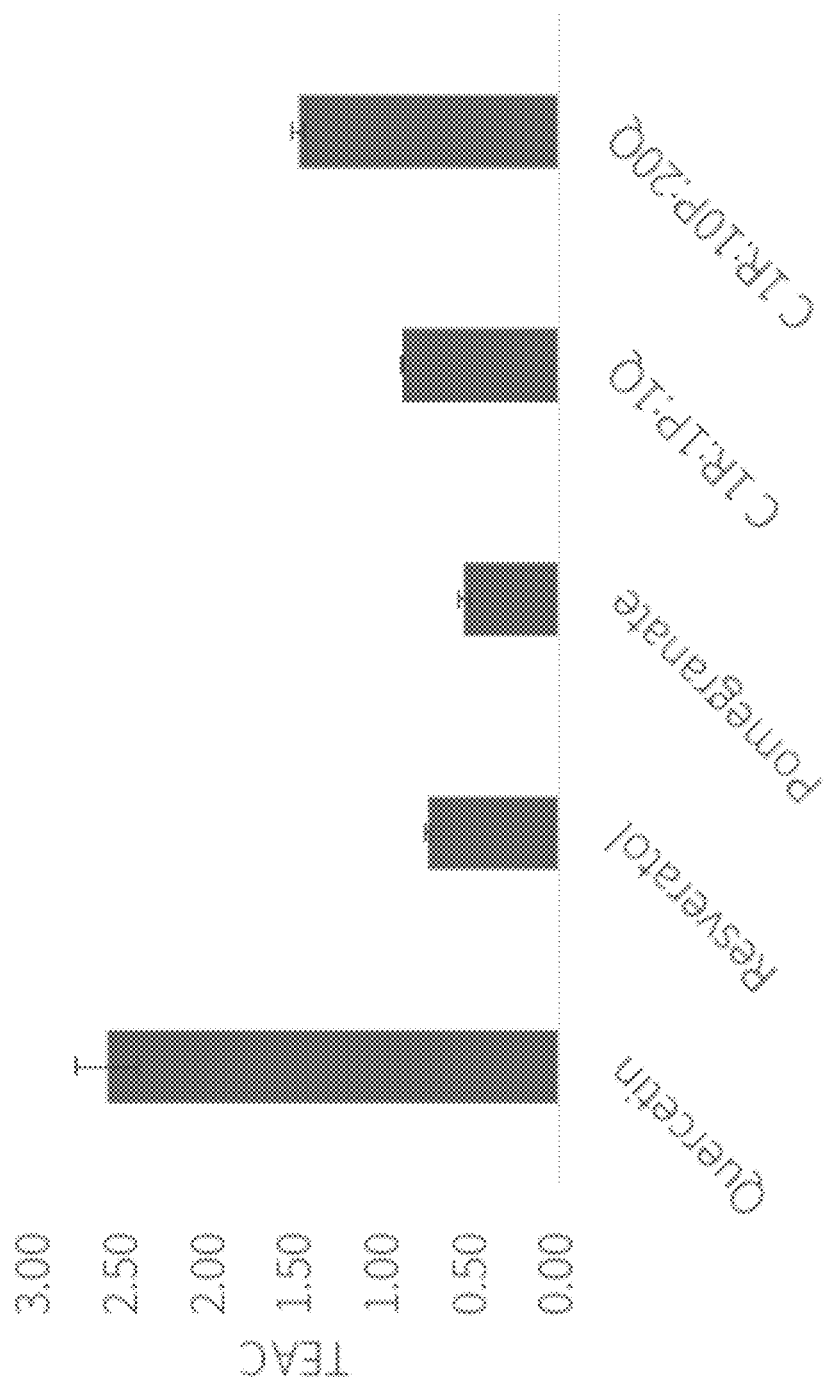
FIG. 2 shows a bar graph displaying the average Trolox equivalent activity (TEAC) values for each antioxidant test group in accordance with one or more embodiments.

An example calibration curve using a range of Trolox standard solutions was plotted (FIG. 1), and the average TEAC values for each test group are shown in FIG. 2. The TEAC values for each of the 3 replicates (sample runs) for each test group is shown in the table of FIG. 3. As shown in FIG. 2, the DPPH antioxidant capacity of the test group having a 1:10:20 mass ratio for resveratrol, pomegranate extract and quercetin (1R:10P:20Q group) as measured by TEAC value was substantially higher than that of the test group having a 1:1:1 mass ratio for resveratrol, pomegranate extract and quercetin (1R:1P:1Q group). Thus, as exemplified in FIG. 2 the administration of resveratrol, pomegranate extract and quercetin in a mass ratio of 1:10:20 (equivalent to administration of resveratrol, ellagic acid, and quercetin in a mass ratio of 1:4:20) results in dramatically increased antioxidative activity as compared with administration of resveratrol, pomegranate extract (40% ellagic acid), and quercetin in a mass ratio of 1:1:1. Accordingly, the combination 1R:10P:20Q group (mass ratio of 1:4:20 for resveratrol, ellagic acid, and quercetin) provides a synergistic antioxidative effect.

Additional Exemplary Embodiments

Additional exemplary embodiments of the liquid and solid compositions of the present application are provided below.
Exemplary Liquid Composition 1 for Dogs and Cats-(Amounts Per 1 mL Dose)
  Quercetin—50 mg
  Ellagic Acid—10 mg
  Resveratrol—2.5 mg Zinc—1 mg
Iron—0.85 mg
Calcium—32 mg
Copper—0.08 mg
Vitamin E—15 IU
Vitamin A—1000 IU
Vitamin D3—100 IU
Iodine—0.014 mg
Niacin—1.42 mg
Potassium—4.2 mg
Manganese—0.28 mg
Methionine—2.85 mg
Phosphorous—16 mg
Magnesium—1.42 mg
Thiamine (vitamin B1)—0.05 mg
Riboflavin (vitamin B2)—0.28 mg
Pantothenic Acid—1.14 mg
Pyridioxide (vitamin B6)—0.11 mg
Folic Acid—0.022 mg
Vitamin B12—0.0022 mg
Ascorbic Acid (vitamin C)—0.07 mg
Additional ingredients: purified water; glycerin; mixed tocopherols, flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Liquid Composition 2 for Dogs and Cats- (Amounts Per 1 mL Dose)
Quercetin-50 mg
Ellagic Acid-10 mg
Resveratrol-2.5 mg
Elderberry-30 mg
Milk Thistle-25 mg
Pumpkin-30 mg
Olive Leaf-25 mg
*Echinacea*-50 mg
Turmeric-5 mg
Additional ingredients: purified water; glycerin; mixed tocopherols, flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Liquid Composition 3 for dogs and cats- (Amounts per 1 mL dose)
Quercetin-50 mg
Ellagic Acid-10 mg
Resveratrol-2.5 mg
*Bifidobacterium Bifidum*
*Lactobacillus Acidophilus*
*Lactococcus Lactis*
*Bifidobacterium Lactis*
Additional ingredients: purified water; glycerin; mixed tocopherols; flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Liquid Composition 4 for dogs and cats- (Amounts per 1 mL dose)
Quercetin-50 mg
Ellagic Acid-10 mg
Resveratrol-3 mg
Glucosamine HCl-125 mg
Methylsulfonylmethane-100 mg
Perna canaliculus-37.5 mg
Chondroitin Sulfate-27.5 mg
Ascorbic Acid-5 mg
Manganese-0.625 mg
Additional ingredients: purified water; glycerin; mixed tocopherols; flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Liquid Composition 5 for dogs and cats- (Amounts per 1 mL dose)
Quercetin-50 mg
Ellagic Acid-10 mg
Resveratrol 2.5 mg
Salmon Oil-1167 mg
Hemp Seed Oil-333 mg
Flax Seed Oil-333 mg
Fish Oil-165 mg
Additional ingredients: purified water; glycerin; mixed tocopherols; flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Liquid Composition 6 for Dogs and Cats- (Amounts Per 1 mL Dose)
Quercetin—50 mg
Ellagic Acid—10 mg
Resveratrol—2.5 mg
Fish Oil—764 mg
Cod Oil—333 mg
EPA—360 mg
GHA—240 mg
Sunflower Seed Oil—233 mg
Hemp Seed Oil—667 mg
Omega 3 Fatty Acids—200 mg
Omega 6 Fatty Acids—450 mg
Additional ingredients: purified water; glycerin; mixed tocopherols; flavoring.

Daily amount of composition by weight of dog or cat:

| Weight | Daily Amount |
| --- | --- |
| Up to 10 lbs | 0.5 mL |
| 10-30 lbs | 1.0 mL |
| 31-65 lbs | 1.5 mL |
| Greater than 65 lbs | 2.0 mL |

Exemplary Solid Composition 1 for Dogs and Cats—Soft Chew (Amounts Per 3.5 Grams)
  Quercetin—50 mg
  Pomegranate extract (containing 70% ellagic acid)—14 mg
  Resveratrol—2.5 mg
  Chamomile—100 mg
  Thiamine Mononitrate—50 mg
  Passion Flower—50 mg
  Ginger—50 mg
  L-Tryptophan—30 mg
  Melatonin—20 mcg
Inactive ingredients: apple cider vinegar, brewers dried yeast, canola oil, dried potato product, flaxseed, glycerin, natural flavoring, rosemary extract, sunflower lecithin, sunflower oil, tapioca starch, mixed tocopherols, water.
Daily amount of composition by weight of dog or cat:

| Weight | Daily Amount |
| --- | --- |
| Up to 25 lbs | 1 soft chew |
| 26-75 lbs | 2 soft chews |
| Greater than 75 lbs | 3 soft chews |

Exemplary Solid Composition 2 for Dogs and Cats—Soft Chew (Amounts Per 5 Grams)
  Quercetin-50 mg
  Pomegranate extract (containing 70% ellagic acid)-14 mg
  Resveratrol-2.5 mg
  Glucosamine HCl (Shellfish Source)-500 mg
  Methylsulfonylmethane (MSM)—400 mg
  *Yucca* schidigera-60 mg
  Chondroitin Sulfate (Porcine Source)—50 mg
  Calcium Ascorbate (Vitamin C)— 50 mg
  Omega-3 Fatty Acids (Fish Oil & Flaxseed)-1,800 mcg
  Omega-6 Fatty Acids (Fish Oil & Flaxseed)—946 mcg
  DL-alpha-tocopheryl acetate (Vitamin E)—50 IU
Inactive ingredients: apple cider vinegar, brewers dried yeast, canola oil, citric acid, sorbic acid, dried potato product, glycerin, mixed tocopherols, natural flavoring, rosemary extract, sunflower lecithin, sunflower oil, tapioca starch, water.
Daily amount of composition by weight of dog or cat:

| Weight | Daily Amount |
| --- | --- |
| Up to 25 lbs | 1 soft chew |
| 26-75 lbs | 2 soft chews |
| Greater than 75 lbs | 3 soft chews |

Exemplary Solid Composition 3 for Dogs and Cats—Soft Chew (Amounts Per 3.5 Grams)
  Quercetin—50 mg
  Pomegranate extract (containing 70% ellagic acid)—14 mg
  Resveratrol—2.5 mg
  Omega-3 Fatty Acids (Fish Oil & Flaxseed)—50 mg
  Turmeric Root—25 mg
  Grape Seed Extract—25 mg
  Pumpkin Powder—25 mg
  Bromelain—25 mg
  EPA (Eicosapentaenoic Acid)—21 mg
  DHA (Docosahexaenoic Acid)—14 mg
Inactive ingredients: apple cider vinegar, brewers dried yeast, canola oil, citric acid, dried potato product, glycerin, mixed tocopherols, natural flavoring, rosemary extract, sunflower lecithin, sunflower oil, tapioca starch, water.
Daily amount of composition by weight of dog or cat:

| Weight | Daily Amount |
| --- | --- |
| Up to 25 lbs | 1 soft chew |
| 26-75 lbs | 2 soft chews |
| Greater than 75 lbs | 3 soft chews |

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

Citation of the references herein are not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

REFERENCES

1. National Cancer Institute. Antioxidants and Cancer Prevention. https://www.cancer.gov/about-cancer/causes-prevention/risk/diet/antioxidants-fact-sheet.
2. Abdullah Shaito et al., Potential Adverse Effects of Resveratrol: A Literature Review. *Int J Mol Sci.* 2020 March; 21(6): 2084.
3. Bahare Salehi et al., Resveratrol: A Double-Edged Sword in Health Benefits. *Biomedicines.* 2018 Sep.; 6(3): 91.
4. Ruiqing Chen, et al. Potential toxicity of quercetin: The repression of mitochondrial copy number via decreased POLG expression and excessive TFAM expression in irradiated murine bone marrow. *Toxicol Rep.* 2014; 1: 450-458.
5. U.S. Pat. No. 10,413,524.
6. U.S. Pat. No. 11,026,917.

7. Leanne M Mathew, et al. Resveratrol administration increases phagocytosis, decreases oxidative burst, and promotes pro-inflammatory cytokine production in healthy dogs. *Vet Immunol Immunopathol.* 2018 September; 203:21-29. doi: 10.1016/j.vetimm.2018.07.013.
8. Natural Dog Health Remedies. Resveratrol Benefits to Dogs. Accessed on Oct. 13, 2021. https://www.natural-dog-health-remedies.com/resveratrol-benefits.html.
9. Katie Woodley, Quercetin for Dogs: Uses and Benefits. Accessed on Oct. 13, 2021. https://www.greatpetcare.com/wellness/quercetin-for-dogs-uses-and-benefits/.
10. M. Saljoughian, PharmD, PhD, Natural Powerful Antioxidants. US Pharm. 2007; 1:HS38-HS42. Published Jan. 23, 2007. https://www.uspharmacist.com/article/natural-powerful-antioxidants.
11. Ask Ariel. Resveratrol for Dogs. Accessed on Oct. 13, 2021. https://www.askariel.com/resveratrol-for-dogs-p/149.htm.
12. Purina. Can Dogs Eat Grapes? Accessed on Oct. 13, 2021. https://www.purina.com/articles/dog/nutrition/can-dogs-eat-grapes.
13. Brendan Howard. Why Grapes & Raisins Are So Dangerous for Dogs. Aug. 24, 2020. https://www.dailypaws.com/dogs-puppies/nutrition/what-can-dogs-eat/can-dogs-eat-grapes.
14. Mary U. Ememe, et al. Evaluation of Resveratrol Supplementation on Laboratory Animals, Cats, Pigs, Horses, Dogs, Cattle, and Birds. Published: Nov. 5, 2018. DOI: 10.5772/intechopen.79104. Accessed at: https://www.intechopen.com/chapters/62407.
15. Rodney Habib. Nature's Benadryl: Quercetin. Apr. 24, 2020. https://www.dogsnaturallymagazine.com/natures-benadryl-quercetin/.
16. RESVANTAGE CANINE—Supplemental Facts & Ingredients. Accessed on Oct. 13, 2021. https://resveratroldogcancer.com/html/ingredients.shtml.
17. Tamara P. Kondratyuk, et al. Evidence supporting the conceptual framework of cancer chemoprevention in canines. *Sci Rep.* 2016; 6: 26500. Published online 2016 May 24. doi: 10.1038/srep26500. 13 pages.
18. National Institutes of Health. Antioxidants: In Depth. Updated: November 2013. https://www.nccih.nih.gov/health/antioxidants-in-depth.
19. The Chocolate Trader. The 5 Proven Health Benefits of Eating Dark Chocolate. Accessed on Oct. 13, 2021. https://thechocolatetrader.com/dark-chocolate-5-health-benefits.

What is claimed is:

1. A method for reducing the oxidative effects of free radicals in an animal subject, the method comprising administering to the animal subject:
   (a) resveratrol in an amount of 1.25 mg-7.5 mg;
   (b) ellagic acid in an amount of 5 mg-30 mg; and
   (c) quercetin in an amount of 25 mg-150 mg,
   wherein the mass ratio of resveratrol:ellagic acid:quercetin administered to the animal subject is 1:4:20.

2. The method of claim 1, wherein the amount of resveratrol is 2.5 mg, the amount of ellagic acid is 10 mg, and the amount of quercetin is 50 mg.

3. The method of claim 1, wherein the amount of resveratrol is 5 mg, the amount of ellagic acid is 20 mg, and the amount of quercetin is 100 mg.

4. The method of claim 1, wherein the animal subject is a cat or a dog.

5. The method of claim 1, wherein the resveratrol, ellagic acid, and quercetin are administered in an ingestible, solid composition.

6. The method of claim 5, wherein the ingestible, solid composition further comprises at least one excipient selected from the group consisting of mixed tocopherols.

7. The method of claim 1, wherein the ellagic acid is administered in the form of a pomegranate extract comprising a concentration of 40% to 70% ellagic acid.

8. A method for reducing the oxidative effects of free radicals in an animal subject, the method comprising administering to the animal subject a liquid composition comprising:
   (a) resveratrol in an amount of 2.5 mg/mL;
   (b) ellagic acid in an amount of 10 mg/mL; and
   (c) quercetin in an amount of 50 mg/mL,
   wherein the mass ratio of resveratrol:ellagic acid:quercetin in the liquid composition 1:4:20.

9. The method of claim 1, wherein the liquid composition is administered at a dosage of 0.5 mL.

10. The method of claim 1, wherein the liquid composition is administered at a dosage of 1.0 mL.

11. The method of claim 1, wherein the liquid composition is administered at a dosage of 1.5 mL.

12. The method of claim 1, wherein the liquid composition is administered at a dosage of 2.0 mL.

13. The method of claim 1, wherein the animal subject is a cat or a dog.

14. The method of claim 6, wherein the liquid composition further comprises at least one excipient selected from the group consisting of mixed tocopherols.

* * * * *